(12) United States Patent
Fukuyama et al.

(10) Patent No.: US 7,666,899 B2
(45) Date of Patent: Feb. 23, 2010

(54) PHARMACEUTICAL COMPOSITION FOR TREATMENT OF LIPID METABOLISM DISORDER

(75) Inventors: Juichi Fukuyama, Tokyo (JP); Masayuki Yamada, Tokyo (JP)

(73) Assignee: Kissei Pharmaceutical, Co. Ltd., Nagano (JP)

( * ) Notice: Subject to any disclaimer, the term of this patent is extended or adjusted under 35 U.S.C. 154(b) by 0 days.

(21) Appl. No.: 11/596,109

(22) PCT Filed: Apr. 27, 2005

(86) PCT No.: PCT/JP2005/008066

§ 371 (c)(1), (2), (4) Date: Dec. 13, 2006

(87) PCT Pub. No.: WO2005/107746

PCT Pub. Date: Nov. 17, 2005

(65) Prior Publication Data

US 2008/0021086 A1 Jan. 24, 2008

(30) Foreign Application Priority Data

May 11, 2004 (JP) .............................. 2004-141634

(51) Int. Cl.
*A61K 31/40* (2006.01)
(52) U.S. Cl. ..................... 514/416; 514/866
(58) Field of Classification Search ................. 514/416, 514/866
See application file for complete search history.

(56) References Cited

U.S. PATENT DOCUMENTS

| 5,202,335 | A | 4/1993 | Sato et al. | |
| 7,390,790 | B2 * | 6/2008 | Jaehne et al. | 514/23 |
| 2003/0040490 | A1 | 2/2003 | Sugiyama et al. | |
| 2004/0034065 | A1 | 2/2004 | Allison et al. | |
| 2004/0192755 | A1 | 9/2004 | Ouchi et al. | |
| 2004/0197400 | A1 | 10/2004 | Ouchi et al. | |
| 2005/0215607 | A1 | 9/2005 | Mikoshiba et al. | |
| 2009/0018181 | A1 | 1/2009 | Mikoshiba et al. | |

FOREIGN PATENT DOCUMENTS

| EP | 1757287 A1 * | 2/2007 |
| WO | WO00/71117 | 11/2000 |

OTHER PUBLICATIONS

Drugs of the Future, "Mitiglinide Calcium Hydrate", 2000, vol. 25, No. 10, p. 1034-1042.
Drugs of the Future, "Endocrine Drugs", N.E. Mealy, et al., 2002, vol. 27, No. 8, p. 799-822.

* cited by examiner

*Primary Examiner*—Kevin Weddington
(74) *Attorney, Agent, or Firm*—Frenkel & Associates, P.C.

(57) ABSTRACT

The present invention provides pharmaceutical compositions for the prevention or treatment of lipid metabolism disorders. The pharmaceutical compositions comprising, as an active ingredient, (2S)-2-benzl-3-(cis-hexahydro-2-isoindolinylcarbonyl)propionic aid (generic name: mitiglinide) or a pharmaceutically acceptable salt thereof, or a hydrate thereof exert remarkable lipid metabolism improving effect, and are useful for, for example, hyperlipidemia such as hypertriglyceridemia of diabetic patients or the like.

8 Claims, No Drawings

PHARMACEUTICAL COMPOSITION FOR TREATMENT OF LIPID METABOLISM DISORDER

TECHNICAL FIELD

The present invention relates to pharmaceutical compositions for the prevention or treatment of lipid metabolism disorders which contain as an active ingredient mitiglinide having chemical structure represented by a formula (Chemical name: (2S)-2-Benzyl-3-(cis-hexahydro-2-isoindolinylcarbonyl)-propionic acid):

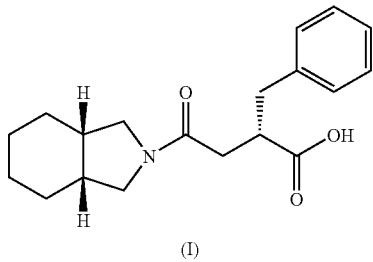

[Chem. 1]

(I)

or pharmaceutically acceptable salts thereof, or hydrates thereof.

BACKGROUND ART

Lipid metabolism disorders are frequent complications of diabetes. The pathological states of lipid metabolism disorders associated with diabetes are complex. Hyperlipidemia such as hypertriglyceridemia mostly seen in men and hypercholesterolemia mostly seen in postmenopausal women is typical, but even in the case of normal lipidemia, qualitative change or abnormality of serum lipoprotein is sometimes found. The lipid metabolism disorder is a major risk factor of macrovascular disorders. Particularly, it is known that increase of triglyceride (TG), total cholesterol (TC), low-density lipoprotein (LDL) cholesterol or remnant lipoprotein, or decrease of high-density lipoprotein (HDL) cholesterol is at high risk of advance to arteriosclerotic diseases, acute pancreatitis, coronary artery disease or the like. Therefore, it is necessary in the treatment of diabetes to pay careful attention to complication such as lipid metabolism disorder like this and prevent or treat it as well as glycemic control.

Similar lipid metabolism disorders also accompany diabetes, impaired glucose tolerance, fasting blood sugar abnormality or the like, and sometimes thyroid hypofunction, obesity, renal disorders such as nephrotic syndrome, hepatobiliary disorders, use of drugs such as adrenal cortical hormone or the like.

The frequency of hyperlipidemia in diabetes differs dependent on success and failure of glycemic control. For example, it has been reported that the frequency of hypertriglyceridemia is high in patients with bad glycemic control. Therefore, glycemic control is also the first therapeutic purpose in diabetic patients with a lipid metabolism disorder (non-Patent Reference 1). However, there are many patients whose lipid metabolism disorders can not be solved despite good glycemic control, and therefore, medication for the lipid metabolism disorder is considered necessary. For example, it has been reported that a single dose of nateglinide, a phenylalanine derivative, suppressed postprandial increase of triglyceride in diabetic patient and is useful for the improvement of postprandial hyperlipidemia (non-Patent Reference 2). In addition, it has been also reported that nateglinide did not show a significant improvement on postprandial lipid variation after 12-week repeated administration compared to pre-treatment (non-Patent Reference 3). Furthermore, it has been reported that a single dose of repaglinide, a benzoic acid derivative, did not show significant improving effect on postprandial lipid variation in diabetic patients compared to placebo (non-Patent Reference 4).

In the treatment of hyperlipidemia associated with diabetes, diet therapy, exercise therapy and lifestyle guidance are performed, and in the case that sufficient improvement is not achieved, medication is administered. As medication, nicotinate derivatives, HMG-CoA reductase inhibitors, anion-exchange resins, fibrates and the like are mainly used (non-Patent Reference 5). However, these drugs can sometimes cause side-effects such as skin disorders, digestive symptoms, enhancement of insulin resistance, hepatic dysfunction, rhabdomyolysis, absorption of drug or the like, which can make it harder for a patient to continue using the drug. Thus, a new drug which can be continuously applicable for diabetic patients has been desired.

Mitiglinide calcium hydrate (chemical name: (2S)-2-benzyl-3-(cis-hexahydro-2-isoindolinylcarbonyl)propionic acid calcium dihydrate) is a commercially available rapid-acting non-sulfonylurea type antidiabetic drug represented by the following formula (II), and is known to correct the condition such as postprandial hyperglycemic state and be useful for glycemic control in Type 2 diabetic patients and the prevention or inhibition of advancing of diabetic complication based on the glycemic control (Patent References 1 to 3). However, it has not ever been reported that mitiglinide improves metabolism disorders of lipids such as triglyceride, cholesterol and the like. It has not been suggested or disclosed that mitiglinide is useful for the prevention or treatment of lipid metabolism disorders such as hyperlipidemia or the like in diabetic patients.

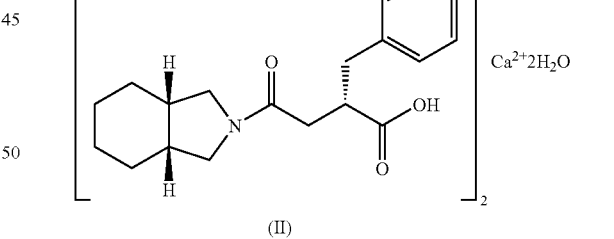

[Chem. 2]

(II)

As mentioned above, it has not ever been known that mitiglinide significantly decreases plasma triglyceride, total cholesterol and the like, and is useful for the prevention or treatment of lipid metabolism disorders such as hyperlipidemia in diabetic patients as described below, and that is not suggested or disclosed in the above references.

Patent Reference 1: Japanese Patent Publication H4-356459;
Patent Reference 2: International Publication WO2004/002473 pamphlet;
Patent Reference 3: International Publication WO2004/002474 pamphlet;
Patent Reference 4: Japanese Patent Publication H6-340622;

Patent Reference 5: Japanese Patent Publication H6-340623;
Non-patent Reference 1: Toshiro Murase, Lipid metabolism disorder, Nippon-Rinsho Extra supplement, Aug. 28, 2002, Vol. 60, Suppl. 8, pp. 145-153;
Non-patent Reference 2: Yutaka Mori, New remedies & therapy (Shin-yaku to Chiryo), 2003, Vol. 53, No. 3, pp. 25-28;
Non-patent Reference 3: Juha Vakkilainen, et. al., Diabetes/Metabolism Research and Reviews, 2002, Vol. 18, pp. 484-490;
Non-patent Reference 4: N. Tentolouris, et. al., Exp Clin Endocrinol Diabetes, 2003, Vol. 111, pp. 370-373;
Non-Patent Reference 5: Joslin's Diabetes Mellitus, Igaku-shoin, pp. 385-389;
Non-Patent Reference: Guidelines for Diagnosis of Atherosclerotic Diseases 2002 edition, Japan atherosclerosis Society, Sep. 30, 2002, pp. 9-17.

DISCLOSURE OF THE INVENTION

Problem to be Solved by the Invention

The object of the present invention is to provide pharmaceutical compositions useful for the prevention or treatment of lipid metabolism disorders such as hyperlipidemia.

Means of Solving the Problems

The present inventors have studied in detail on clinical pharmaceutical characteristics of a pharmaceutical composition containing as an active ingredient mitiglinide calcium hydrate represented by the above formula (II), and found that the pharmaceutical composition has an effect remarkably lowering lipids such as plasma triglyceride, total cholesterol, LDL cholesterol or the like, or remarkably increasing HDL cholesterol level and is extremely useful for the prevention or treatment of lipid metabolism disorders such as hyperlipidemia or the like, thereby forming the basis of the present invention.

The present invention relates to a pharmaceutical composition useful for the prevention or treatment of lipid metabolism disorders such as hyperlipidemia. For more detail, the present invention relates to:

[1] a pharmaceutical composition for the prevention or treatment of a lipid metabolism disorder, which comprises as an active ingredient mitiglinide represented by the above formula (I) or a pharmaceutically acceptable salt thereof, or a hydrate thereof;

[2] a pharmaceutical composition as described in the above [1] wherein the lipid metabolism disorder is a disorder associated with one or more selected from a group consisting of diabetes, impaired glucose tolerance and fasting blood sugar abnormality;

[3] a pharmaceutical composition as described in the above [2] wherein the lipid metabolism disorder is a disorder associated with diabetes;

[4] a pharmaceutical composition as described in any one of the above [1] to [3] wherein the lipid metabolism disorder is one or more selected from a group consisting of hyperlipidemia, hypertriglyceridemia, hypercholesterolemia, hyper-LDL-cholesterolemia, hypoHDL-cholesterolemia, and postprandial hyperlipidemia;

[5] a pharmaceutical composition as described in any one of the above [1] to [5] wherein the active ingredient is mitiglinide calcium hydrate; and the like.

The present inventors analyzed changes in laboratory values of lipids in patients who had a lipid metabolism disorder before the treatment was started (lipid metabolism disorder group) using clinical results of mitiglinide calcium hydrate in Type 2 diabetic patients, and evaluated the improving efficacy of the compound.

As a result, it was found that the present compound exerts a remarkable effect improving the lipid metabolism disorder such as hyperlipidemia, for example, effects such as significantly lowering plasma TG, TC and LDL-cholesterol and increasing HDL-cholesterol compared to pretreatment.

The lipid metabolism disorder in the scope of the present invention includes the state with higher blood lipid level than normal level (hyperlipidemia), qualitative change and abnormality in blood lipoprotein and increase of free fatty acid. In particular, as hyperlipidemia, hypercholesterolemia, hyper-LDL-cholesterolemia, hypo-HDL-cholesterolemia, hypertriglyceridemia and the like can be illustrated. As examples, a lipid metabolism disorder associated with diabetes is preferable, and hypercholesterolemia, hypertriglyceridemia which are associated with diabetes are more preferable. In addition, hyperlipidemia includes postprandial hyperlipidemia.

In the present invention, the term "hyperlipidemia" basically means a state wherein total cholesterol level is 200 mg/dL or more, LDL-cholesterol level is 120 mg/dL or more, HDL-cholesterol level is less than 40 mg/dL or triglyceride level is 150 mg/dL or more, although the diagnosis criteria may change according to predisposition, complications, course of disease of each patient and the like (see the above non-Patent Reference 6).

Mitiglinide represented by the above formula (I) or a pharmaceutically acceptable salt thereof, or a hydrate thereof can be easily prepared according to method described in literature or an analogous method thereof (for example, see the above Patent References 1, 4 and 5).

As the pharmaceutically acceptable salt of mitiglinide represented by the above formula (I), a salt with an inorganic base such as sodium salt, potassium salt, calcium salt or the like, a salt with an organic amine or amino acid such as morpholine, piperidine, phenylalaninol or the like can be illustrated. A calcium salt is preferable. In addition, as an active ingredient of the present invention, mitiglinide calcium hydrate represented by the above formula (II) is the most preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

The pharmaceutical compositions of the present invention can be prepared by suitably admixing with or by diluting and dissolving with an appropriate pharmaceutical additive pharmaceutically used depending the dosage form such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional methods. In the case of the uses in combination with other drug(s), they can be prepared by formulating each active ingredient together or individually in a similar manner as defined above.

For example, powders can be formulated by, if desired, admixing well a compound of the present invention with appropriate excipients, lubricants and the like.

For example, tablets can be easily prepared in a method described in literature or an analogous method (see the above Patent References 2 and 3). The tablets, further if desired, can be suitably coated to provide film-coated tablets, sugar-coated tablets, enteric-coated tablets and the like.

For example, capsules can be formulated by, if desired, admixing well a compound of the present invention with appropriate excipients, lubricants and the like and filling it in appropriate capsules. Furthermore, it is also applicable to formulate granules or fine-powders in accordance with conventional methods, and then fill the compositions in capsules.

Furthermore, the compounds of the present invention can be also used in combination with other hypoglycemic drugs or drugs for the treatment of diabetic complication. Examples of the other hypoglycemic drug which can be used in combination with include, for example, an insulin sensitivity enhancers such as pioglitazone hydrochloride, rosiglitazone maleate or the like, a glucose absorption inhibitor such as voglibose, acarbose, miglitol or the like, biguanides such as metformin hydrochloride, buformin hydrochloride or the like, an insulin secretion enhancer such as tolbutamide, acetohexamide, tolazamide, glyclopyramide, glybuzole, glyburide/glibenclamide, gliclazide, glimepiride or the like, an insulin preparation and the like. In addition, examples of the other drug for the treatment of diabetic complications which can be used in combination with include, for example, an aldose reductase inhibitor such as epalrestat or the like, a sodium channel antagonist such as mexiletine hydrochloride or the like, an angiotensin converting enzyme inhibitor such as imidapril hydrochloride, lisinopril or the like, an angiotensin II receptor antagonist such as losartan potassium, irbesartan or the like) and the like.

In addition, the compounds of the present invention can be also used in combination with other hypolipidemic drugs. Examples of the other hypolipidemic drug which can be used in combination with include, for example, a nicotinate derivative, a HMG-CoA reductase inhibitor such as pravastatin, simvastatin, atorvastatin, fluvastatin or the like, an anion-exchange resin such as colestylamine, colestimide or the like, a fibrate agent such as bezafibrate, fenofibrate or the like, probucol and the like.

In the case of uses of the compound of the present invention in combination with the above one or more other drugs, the present invention includes either dosage form of simultaneous administration as a single preparation or separated preparations in way of the same or different administration route, and administration at different dosage intervals as separated preparations in way of the same or different administration route.

When the pharmaceutical compositions of the present invention are employed in the practical treatment, the dosage of a compound of the present invention as the active ingredient is appropriately decided depending on the body weight, age, sex presence or absence of complication, and degree of diseases or treatment of each patient, and as a dose of mitiglinide calcium hydrate, which is approximately within the range of from 5 to 45 mg, preferably approximately within the range of from 5 to 22 mg, more preferably approximately within the range of from 10 to 22 mg as a single dose. As an administration method, administration three times before meal is essentially preferable. Also, in the case of the uses in combination with the above other drug(s), the dosage of the compound of the present invention can be decreased depending on the dosage of the other drug(s).

Effect of the Invention

The pharmaceutical compositions of the present invention exert an excellent improving effect on lipid metabolism disorders in diabetic patients. The present invention can provide a pharmaceutical composition useful for the prevention or treatment of lipid metabolism disorders such as hyperlipidemia or the like.

BEST MODE TO PRACTICE THE INVENTION

The present invention is further illustrated in more detail by way of the following Example. However, the present invention is not limited thereto.

Example 1

Clinical Efficacy on Lipid Metabolism Disorders in Diabetic Patients

The following clinical study was conducted in Type 2 diabetic patients using tablets containing 5 mg of mitiglinide calcium hydrate and tablets containing 10 mg of mitiglinide calcium hydrate.

Patients included: Type 2 diabetic patients;

Mode of dosing: oral administration of 5 to 20 mg as a single dose three times per day just before (5 minutes before) each meal;

Dosing period: 28 weeks to 52 weeks;

Major items of observation: stabilized hemoglobin A1c (HbA1c), biochemical examination of blood (total cholesterol, triglyceride, LDL-cholesterol, HDL-cholesterol, free fatty acid);

Statistical Method: in all patients with an abnormal value of each lipid at pretreatment and without any hypolipidemic agent, significance test was conducted on the average of the final evaluation against the average of the pretreatment (*: $P<0.05$, **: $P<0.01$).

(1) Changes in Serum Triglyceride (TG)

Patients with 150 mg/dL or more of serum TG at pretreatment were picked out as an abnormal group, the efficacy of mitiglinide calcium hydrate was evaluated on the group. The result is shown in Table 1.

TABLE 1

| Patients for | Average of TG (mg/dL) | |
| --- | --- | --- |
| Analysis | Pretreatment | Final evaluation |
| All patients with 150 mg/dL or more of pretreatment TG | 262.6 | 216.3** |

(2) Changes in Serum Total Cholesterol (TC)

Patients with 200 mg/dL or more of serum TC at pretreatment were picked out as an abnormal group, the efficacy of mitiglinide calcium hydrate was evaluated. The result is shown in Table 2.

TABLE 2

| Patients for | Average of TC (mg/dL) | |
| --- | --- | --- |
| Analysis | Pretreatment | After the end of administration |
| All patients with 200 mg/dL or more of TC | 231.8 | 226.4* |

(3) Changes in Abnormal Values of Other Lipids

Patients with 0.86 mEq/L or more of serum free fatty acid (FFA), 120 mg/dL or more of LDL-cholesterol (LDL-C) and less than 40 mg/dL of HDL-cholesterol at pretreatment, respectively, were picked out as abnormal groups, the efficacy of mitiglinide calcium hydrate was evaluated. The result is shown in Table 3.

TABLE 3

| Patients for Analysis | Lipid | Average | |
|---|---|---|---|
| | | Pretreatment | After the end of administration |
| Patients with 0.86 mEq/L or more of FFA | FFA (mEq/L) | 1.021 | 0.745** |
| Patients with 120 mg/dL or more of LDL-C | LDL-C (mg/dL) | 144.9 | 137.7** |
| Patients with less than 40 mg/dL of HDL-C | HDL-C (mg/dL) | 34.7 | 40.3** |

From patients having been enrolled in the above the above clinical study described in the above Example 1, concrete examples are given as follows.

Example 2

A 59-year-old woman. The doses were 10 mg at a time from the start of dosing till 16th week, and increased to 20 mg after 16th week. The values of TC, LDL-C and FFA at pretreatment were 240 mg/dL, 137 mg/dL and 0.94 mEq/L, respectively. At the final evaluation after 52-week administration, TC, LDL-C and FFA were 185 mg/dL, 108 mg/dL and 0.26 mEq/L, respectively. The changes of TC, LDL-C and FFA were −55 mg/dL, −29 mg/dL and −0.68 mEq/L, respectively, and that was remarkable improvement.

Example 3

A 54-year-old man. The dose was 10 mg through the administration period. TG at pretreatment was a high value of 171 mg/dL. At the final evaluation after 52-week administration, TG was 110 mg/dL, the change was −61 mg/dL, and that was a remarkable improvement.

Example 4

A 47-year-old woman. The doses were 10 mg at a time from the start of dosing till 16th week, and increased to 20 mg after 16th week. The values of TG and TC at pretreatment were 163 mg/dL and 214 mg/dL, respectively. At the final evaluation after 40-week administration, TG and TC were 101 mg/dL and 162 mg/dL, and the changes were −62 mg/dL and −52 mg/dL, respectively, and these were remarkable improvement.

Example 5

A 62-year-old man with concomitant hyperlipidemia. The doses were 10 mg at a time from the start of dosing till 16th week, and increased to 20 mg after 16th week. The values of TG and FFA at pretreatment were 213 mg/dL and 0.53 mEq/L, respectively. At the final evaluation after 24-week administration, TG and FFA were 145 mg/dL and 0.30 mEq/L, and the changes were −68 mg/dL and −0.23 mEq/L, respectively, and these were remarkable improvement.

Example 6

A 37-year-old man with concomitant hyperlipidemia. The dose was 10 mg through the administration period. The values of TC and LDL-C at pretreatment were 260 mg/dL and 149 mg/dL, respectively. At the final evaluation after 52-week administration, TC and LDL-C were 203 mg/dL and 134 mg/dL, and the changes were −57 mg/dL and −15 mg/dL, respectively, and these were remarkable improvement.

Example 7

A 64-year-old woman. The dose was 10 mg through the administration period. The values of TG, TC, LDL-C and HDL-C at pretreatment were 170 mg/dL, 226 mg/dL, 129 mg/dL and 57 mg/dL, respectively. At the final evaluation after 52-week administration, TG, TC, LDL-C and HDL-C were 100 mg/dL, 206 mg/dL, 116 mg/dL and 72 mg/dL, and the changes were −70 mg/dL, −20 mg/dL, −13 mg/dL and +15 mg/dL, and these were remarkable improvement.

As mentioned above, it was shown that in the clinical study using mitiglinide calcium hydrate for diabetic patients, the compound of the present invention exerts remarkable effects to lower TG, TC, LDL-C or FFA, or increase HDL-C in patients with high blood TG, blood TC, FFA or LDL-C, or low HDL-C.

INDUSTRIAL APPLICABILITY

The pharmaceutical compositions of the present invention exert effects to suppress the increase of lipids such as serum TG, TC, LDL-C and the like or increase HDL-C, and are extremely useful as an agent for the prevention or treatment of lipid metabolism disorders such as hyperlipidemia or the like.

The invention claimed is:

1. A method for the treatment of a lipid metabolism disorder wherein the lipid metabolism disorder is hyperlipidemia, which consists essentially of administering a therapeutically effective amount of mitiglinide or a pharmaceutically acceptable salt thereof, or the calcium hydrate thereof.

2. A method for the treatment claimed in claim 1 wherein the lipid metabolism disorder is a disorder associated with one or more selected from a group consisting of type II diabetes, impaired glucose tolerance and fasting blood sugar abnormality.

3. A method for the treatment claimed in claim 2 wherein the lipid metabolism disorder is a disorder associated with type II diabetes.

4. A method for the treatment claimed in any one of claims 1 to 3 wherein the lipid metabolism disorder is one or more selected from a group consisting of hypertriglyceridemia, hypercholesterolemia, hyperLDL-cholesterolemia and hypo-HDL-cholesterolemia.

5. A method for the treatment claimed in claim 4, which consists essentially of administrating a therapeutically effective amount of mitiglinide calcium hydrate.

6. A method for the treatment claimed in claim 5, which consists essentially of orally administering 10 to 22 mg three times daily of mitiglinide calcium hydrate.

7. A method for the treatment claimed in claim 5, which comprises administering for 6 months or more.

8. A method for the treatment claimed in claim 6, which comprises administering for 6 months or more.

* * * * *